United States Patent
Arimoto

[11] Patent Number: 5,756,128
[45] Date of Patent: May 26, 1998

[54] AGRICULTURAL CHEMICAL PREPARATIONS AND METHOD FOR PREPARING SAME

[75] Inventor: Yutaka Arimoto, Wako, Japan

[73] Assignee: Rikagaku Kenkyusho, Saitama-Ken, Japan

[21] Appl. No.: 776,720

[22] PCT Filed: Aug. 2, 1995

[86] PCT No.: PCT/JP95/01535

§ 371 Date: Jan. 31, 1997

§ 102(e) Date: Jan. 31, 1997

[87] PCT Pub. No.: WO96/03872

PCT Pub. Date: Feb. 15, 1996

[30] Foreign Application Priority Data

Aug. 2, 1994 [JP] Japan .................... 6-181550

[51] Int. Cl.$^6$ .................... A01N 59/02; A01N 37/02; A01N 37/06; A01N 25/30
[52] U.S. Cl. .................... 424/705; 424/703; 424/713; 514/546; 514/547; 514/549; 514/552; 514/785; 514/786
[58] Field of Search .................... 424/630, 637, 424/638, 703, 705, 713, 785, 786; 514/546, 547, 549, 552

[56] References Cited

U.S. PATENT DOCUMENTS

5,362,707  11/1994  Fiard et al. .................... 504/234

FOREIGN PATENT DOCUMENTS

| | | |
|---|---|---|
| 0456198 A1 | 11/1991 | European Pat. Off. . |
| 0498785 A1 | 8/1992 | European Pat. Off. . |
| 59193803 A | 11/1984 | Japan . |
| 63233902 | 9/1988 | Japan . |
| 63233902 A | 9/1988 | Japan . |
| 06145003 A | 5/1994 | Japan . |
| 2252499 | 8/1992 | United Kingdom . |

*Primary Examiner*—John Pak
*Attorney, Agent, or Firm*—Seed and Berry LLP

[57] ABSTRACT

Disclosed are an agricultural chemical preparation which comprises 100 parts by weight of a fatty acid ester of an aliphatic polyhydric alcohol, 10 to 2000 parts by weight of an agricultural effective component and 10 to 400 parts by weight of a surfactant and a method for preparing the same. The agricultural chemical preparation sufficiently shows its efficacy even at a low concentration and exhibits not only preventive effect, but also curative effect.

13 Claims, No Drawings

AGRICULTURAL CHEMICAL PREPARATIONS AND METHOD FOR PREPARING SAME

This application is a 371 of PCT/JP95/01535, filed on Aug. 2,1995.

1. Technical Field

The present invention relates to an agricultural chemical preparation which can sufficiently show its efficacy even when it is used in a concentration lower than that conventionally used as well as a method for preparing the same.

2. Background Art

As agricultural chemicals, there have widely been used those comprising, as effective components, inorganic compounds such as copper compounds, mercury compounds and arsenic compounds; and organic compounds such as organic chlorine compounds and organic phosphorus compounds and these agricultural chemicals have contributed to a production increase of farm products. However, most of these agricultural chemicals act not only on the intended diseases and harmful insects, but also on beneficial insects and human beings and accordingly, there have been pointed out a bad influence thereof on human bodies and damage of environment.

Under such circumstances, Japanese Un-Examined Patent Publication (hereinafter referred to as "J. P. KOKAI") No. Sho 63-233902 an agricultural chemical preparation which can be used in a low dose as compared with previously used agricultural chemical preparations while ensuring the effect of controlling diseases and/or harmful insects to an extent comparable to that achieved by the previous agricultural chemical preparations and which would not be accompanied by any environmental pollution as well as a method for preparing the preparation.

However, this method requires the use of a volatile organic solvent such as ethanol and propanol as a solvent for dissolving a fatty acid ester of an aliphatic polyhydric alcohol during the production processes. There is a high possibility of causing an explosion or a fire if these organic solvents are volatilized during the processes for the production of such an agricultural chemical preparation and therefore, this method suffers from a serious problem from the practical standpoint.

In addition, these organic solvents must also be used for forming a stable aqueous emulsion of an agricultural chemical which comprises an agricultural effective component and a fatty acid ester of an aliphatic polyhydric alcohol prior to the spray of the agricultural chemical on farm products and it is impossible to form a uniform aqueous emulsion from a product comprising the foregoing components, which has been stored over a long time period after the production thereof and from which the foregoing organic solvents are lost through evaporation, when preparing a liquid formulation to be sprayed.

On the other hand, an agricultural chemical purchased by a farm household is seldom used up within a specific time period and accordingly, the rest is often stored while the sealed container is left open. In such case, the organic solvents required for the formation of the foregoing emulsion are lost through volatilization. Accordingly, the spraying solution prepared from such an agricultural preparation does not show its effect and the use of such a spraying solution becomes a cause of spray injury.

The foregoing preparation has not yet been practically used because of the foregoing problems concerning the preparation thereof.

DISCLOSURE OF THE INVENTION

It is an object of the present invention to provide an agricultural chemical preparation which can sufficiently show its efficacy even when it is used in a concentration lower than that of the corresponding agricultural chemical preparation conventionally used.

Another object of the present invention is to provide an agricultural chemical preparation having preventive and curative effects.

A still another object of the present invention is to provide a method for preparing the foregoing agricultural chemical preparations without using any volatile organic solvent such as ethanol and propanol.

The foregoing objects of the present invention can be accomplished by providing an agricultural chemical preparation which comprises 100 parts by weight of a fatty acid ester of an aliphatic polyhydric alcohol, 10 to 2000 parts by weight of an agricultural effective component and 10 to 400 parts by weight of a surfactant. This agricultural chemical preparation can be prepared by dissolving 100 parts by weight of a fatty acid ester of an aliphatic polyhydric alcohol and 10 to 400 parts by weight of a surfactant with warming; then adding 10 to 2000 parts by weight of an agricultural effective component thereto; mixing these components; and stirring the resulting mixture.

As aliphatic polyhydric alcohols constituting the fatty acid esters of aliphatic polyhydric alcohols, there may be mentioned saturated and unsaturated aliphatic polyhydric alcohols having 3 to 6 carbon atoms. Specific examples thereof are glycerin, propylene glycol, sorbitol and sorbitan. On the other hand, as fatty acid moieties thereof, there may be mentioned those constituting one or more fatty acids, for instance, saturated fatty acids such as caprylic acid, capric acid, lauric acid, myristic acid, palmitic acid, stearic acid, arachic acid and behenic acid, or unsaturated fatty acids such as oleic acid, linoleic acid, linolenic acid and ricinoleic acid having 8 to 22 carbon atoms; and mixed fatty acids, for instance, natural animal and vegetable oils such as tallow, cottonseed oil, rapeseed oil and hardened oil.

The fatty acid esters of aliphatic polyhydric alcohols usable in the present invention are, for instance, mono-, di-or triesters obtained from the foregoing aliphatic polyhydric alcohols and the foregoing fatty acids according to the usual methods such as esterification or transesterification. Specific examples thereof suitably used herein are sorbitan monolaurate, sorbitan monostearate, glycerin monooleate, glycerin monooctanoate, triglycerin monooleate, glycerin monopalmitate, glycerin monosoybeen oil-derived fatty acid ester, glycerin monocottonseed oil-derived fatty acid ester and polyglycerin fatty acid ester.

The agricultural effective components which can be used in the present invention are not restricted to specific ones and accordingly, there may be used, for instance, various kinds of agricultural and horticultural fungicides, insecticides and herbicides so far as they are in solid powdery state at ordinary temperature. Those insoluble in water may likewise be used, but those soluble in water are generally used preferably. Specific examples of such agricultural effective components are currently used agricultural chemicals such as copper 8-oxyquinoline, copper nonylphenol sulfonate, copper terephthalate, basic copper sulfate, basic copper chloride, cupric chloride, basic copper carbonate, methyl 1-(butylcarbamoyl)-2-benzimidazole carbamate, antibiotic-polyoxin complex, o,o-diethyl-s-benzylthiophosphate, 2-sec-butylphenyl-N-methyl carbamate, o,o-dimethyl-2,2,2-trichloro-1-hydroxyethylphosphate, as well as sodium hydrogen carbonate, sodium carbonate, potassium hydrogen carbonate and potassium carbonate, which are highly safe to animals and vegetables.

Further, the agricultural chemical preparation of the present invention may comprise an organic acid such as citric acid, acetic acid, oxalic acid, malic acid or adipic acid, in addition to the foregoing agricultural effective component. Particularly preferred are those each comprising a combination of the foregoing copper compound and an organic acid such as citric acid or adipic acid. The amount of the organic acid to be incorporated into the preparation preferably ranges from 10 to 400 parts by weight and more preferably 50 to 200 parts by weight per 100 parts by weight of the agricultural effective component.

When sulfur is used as the effective component for the agricultural chemical preparation (hereinafter referred to as "agricultural effective component"), powdery sulfur is used and preferably comprises fine particles of not less than 200 mesh pass, in particular, not less than 500 mesh pass while taking into consideration the dispersion stability in a spray.

The sulfur content of the agricultural chemical preparation preferably ranges from about 10 to about 60% by weight, in particular, 20 to 50% by weight while taking into consideration the fact that it would be diluted 500 to 2000 times with water.

In the present invention, the amount of the agricultural effective component relative to that of the aliphatic polyhydric alcohol-fatty acid ester ranges from 10 to 2000 parts by weight and preferably 100 to 1000 parts by weight per 100 parts by weight of the ester. This is because if the amount of the agricultural effective component is less than 10 parts by weight, the concentration thereof is too low to expect the achievement of a sufficient effect thereof and any satisfactory emulsion cannot be prepared. On the other hand, the amount thereof is greater than 2000 parts by weight, the resulting preparation does not provide any desired emulsion when being diluted with water prior to the practical use thereof.

Surfactants to be used in the present invention are not restricted to any specific one so far as they possess functions peculiar thereto and they can be selected from, for instance, non-ionic surfactants, anionic surfactants and cationic surfactants, particularly preferred being non-ionic surfactants and anionic surfactants. Specific examples thereof include non-ionic surfactants such as polyoxyethylene alkyl ether, polyoxyethylene alkylallyl ether, polyoxyethylene alkylphenyl ether, polyoxyethylene alkylamine, alkyldihydroxyalkylamine, polyoxyethylene bisphenyl ether and polyoxyethylene alkyl ester; anionic surfactants such as polyoxyethylene alkyl ether sulfate, polyoxyethylene alkylphenyl ether sulfate, dialkyl-sulfosuccinate, alkylbenzenesulfonate, alkyl diphenyl ether disulfonate, lignin sulfonate, N-methyl fatty acid sarcosinate and polyoxyethylene alkyl ether phosphate; and cationic surfactants. In addition, usable herein also include phospholipids such as vegetable lecithin, yolk lecithin, phosphatidyl choline, phosphatidyl ethanolamine and phosphatidyl inositol.

The amount of the surfactant relative to that of the aliphatic polyhydric alcohol-fatty acid ester ranges from 10 to 400 parts by weight and preferably 50 to 300 parts by weight per 100 parts by weight of the ester. This is because if the amount of the surfactant is less than 10 parts by weight, the concentration thereof is too low to achieve a sufficient emulsifying effect thereof and any effective emulsion cannot be prepared. On the other hand, it is not necessary for the emulsification to use the surfactant in an amount greater than 400 parts by weight and the use thereof in such a large amount rather becomes a cause of phytotoxicity.

The agricultural chemical preparation of the invention may, if necessary, comprise an appropriate thickener in addition to the foregoing essential components. Such thickening agents may be, for instance, powdery inorganic compounds. Specific examples thereof are white carbon, talc and diatomaceous earth.

Moreover, the agricultural chemical preparation of the present invention may likewise comprise, for instance, other powdery naturally occurring substances and/or saccharides and specific examples thereof include gum arabic, lactose and sorbitol.

The agricultural chemical preparation of the present invention can be prepared by, for instance, dissolving 100 parts by weight of an aliphatic polyhydric alcohol-fatty acid ester and 10 to 400 parts by weight of a surfactant, with warming at a temperature preferably ranging from 30° to 80° C., then adding 10 to 2000 parts by weight of an agricultural effective component to the resulting mixture, uniformly admixing these ingredients and sufficiently stirring the mixture.

The present invention permits the elimination of the use of solvents such as $C_1$ to $C_3$ alcohols and/or propylene glycol which are required for the preparation of the agricultural chemical preparations disclosed in J. P. KOKAI No. Sho 63-233902. In addition, the present invention also permits the use of water as a solvent (water cannot be used in the conventional method) and this accordingly permits the preparation of agricultural chemical preparations which include, as agricultural effective components, not only those in powdery states at ordinary temperature, but also those in liquid states at ordinary temperature. Furthermore, the present invention permits the production of various preparations in various dosage forms including not only the suspension concentrate (the foregoing conventional techniques permits the production of only the suspension concentrate), but also wettable powders, dust formulations or the like, depending on purposes. Moreover, the present invention allows the elimination of the use of installations for recovering organic solvents and explosion-proof installations and thus permits easy production of the agricultural preparation and reduction of the production cost since the method of the present invention does not require the use of any organic solvent such as an alcohol during the production steps.

Moreover, the conventional agricultural preparations are considerably impaired in the solubility which is required when preparing a spray, if the volatile components in the agricultural preparation such as organic solvents are lost through evaporation, but the agricultural preparation of the present invention does not include any such volatile component and accordingly, the solubility of the preparation of the present invention is never deteriorated with time. For instance, the conventional agricultural preparation which is partially used and stored over a certain time period cannot be used since it is not satisfactorily dispersed or suspended in water, but the agricultural preparation of the invention maintains its good dispersibility in water identical to that observed for the preparation immediately after opening the sealed container of the preparation even when it is stored over a considerable time period.

More specifically, the conventional method for preparing the agricultural preparations suffers from two fatal drawbacks, i.e., those concerning a danger encountered during the preparation and the stability of the resulting preparation. For this reason, the conventional method has not yet been used practically, although the preparation per se has been proved to be effective. The present invention permits the complete elimination of the foregoing two drawbacks.

Moreover, the preparation of the present invention shows a novel effect which cannot be expected in the light of the conventional agricultural chemicals. For instance, the inorganic copper compounds show a high effect of controlling diseases of plants, but the use thereof is accompanied by strong phytotoxicity of plants. The effect of the inorganic copper compound is mainly achieved due to the presence of copper ions and, upon practical use, the release of copper ions are usually suppressed by making the preparation alkaline. The pH control is carried out in order to prevent the occurrence of any phytotoxicity which is believed to be also caused due to the presence of copper ions. However, the pH value of the conventional agricultural preparation during practical use is controlled to an alkaline region on the order of 10 to 11, to thus completely eliminate any danger of causing phytotoxicity. The copper compound does not release any copper ion at that pH region and therefore, the conventional inorganic copper preparations show the ability to control diseases completely because of the presence of an alkali.

Among the conventional inorganic copper preparations, there has been known a preparation prepared by controlling the copper ion concentration in such a manner that the spray prepared from the preparation has a copper ion concentration which is effective for controlling the growth of pathogenic organisms, but does not cause any phytotoxicity, while taking note of the fact that the copper concentration at which phytotoxicity is caused is higher than that required for controlling the growth of pathogenic organisms. In this case, the copper compound is formed into a preparation along with sodium hydrogen carbonate while noticing the pH-dependency of the dissociation of copper into copper ions. However, copper sulfate undergoes a reaction with sodium hydrogen carbonate in the presence of water to thus give carbon dioxide gas. Therefore, one must devise a measure to prevent the water absorption of the preparation and accordingly, extreme care must be taken during processes for producing the preparation and during packaging the same after the production. Moreover, the product undergoes a reaction through absorption of the water in air after opening the package. Various problems arise upon practical use. For instance, the foregoing absorption of water makes the storage of the preparation difficult and one must always use up the preparation in a sealed container once opened.

The preparations obtained in Examples 1 and 2 according to the present invention comprise, as principal components, copper sulfate and copper chloride respectively, but any alkaline compound is not used during the processes for preparing the preparations. For this reason, the preparations never generate carbon dioxide during and after the production thereof and this accordingly makes operations such as packaging simple and permits the storage of the preparation even after opening the sealed container thereof.

In addition, it has been found out that if a preparation comprising an inorganic copper compound such as a copper sulfate solution is admixed with plant's components such as proteins and/or amino acids, the disease controlling effect of the preparation is considerably deteriorated, but the addition of, for instance, glycerin fatty acid ester, citric acid and/or adipic acid to the preparation markedly inhibits such reduction in the disease controlling effect of the preparation. The preparations obtained in Examples 1 and 2 according to the present invention show high controlling effects on pathogenic organisms within lesions and dead branches on which the conventional preparations comprising inorganic copper compounds are not effective. This is because the ability of the preparation according to the present invention to control diseases is not affected by the plant's components derived from such lesions and dead branches.

Moreover, inorganic sulfur has already been used as an effective component for agricultural fungicides and it has also been known that the inorganic sulfur preparation exhibits a high effect of preventing various kinds of powdery mildew. However, the conventional sulfur agricultural chemical preparations (commercially available products) never have an effect of curing powdery mildew. The term "preventive effect (effect of preventing)" herein used means the effect of preventing disease, observed when a sulfur preparation is sprayed on a plant such as leaves of cucumber plants and then conidia of a causal fungus are inoculated upon the leaves. Contrary to this, the term "effect of curing (curative effect)" herein used means the effect of killing causal fungi observed when a sulfur preparation is sprayed on a plant such as leaves of cucumber plants after a plant is attacked with a disease or after the leaves of cucumber plants are attacked with powdery mildew. The conventional sulfur agricultural chemical preparations (commercially available products) are excellent in the preventive effect, but do not show any curative effect at all. On the contrary, the agricultural chemical preparations obtained in Examples 3a and 3b according to the present invention show not only the effect of preventing powdery mildew comparable to that observed for the conventional preparations, but also an extremely high effect of curing the leaves of cucumber plants suffering from powdery mildew.

Moreover, the organic copper agricultural chemical preparation obtained in Example 4 according to the present invention exhibits a novel controlling effect which has never been achieved by the conventional agricultural chemical preparations mainly comprising organic copper compounds. More specifically, mulberry trees are in general infected with *Diaporthe nomurai* HARA in the summer season, the furgus are latent and the branches of the mulberry trees are recurred by the latent furgus in the next spring when the mulberry trees are buried under snow in the winter season over not less than 80 days. The agent is sprayed before snow falls and the effect thereof should last till the next spring. An organic copper preparation (Altaber suspension concentrate) prepared by the conventional method not only does not have any effect of controlling the disease at all, but also becomes a cause of phytotoxicity of mulberry trees and as a result, a large amount of branches thereof are dead as compared with those which are dead due to disease. On the other hand, the organic copper preparation obtained in Example 4 can almost completely suppress the development of die-back of mulberry trees and does not cause any phytotoxicity. Incidentally, each of the organo-copper, glycerin-fatty acid ester and organic acids which are ingredients for the novel preparation as well as a combination of an organic-copper with an organic acid do not show any effect of controlling this disease at all.

Moreover, regarding perennial crops such as fruit trees, pathogenic organisms overwinter on the trees, they are active as it is getting warmer in the next spring and the buds are infected with the organisms to thus cause disease. For this reason, if an agricultural chemical is sprayed on the plant before the organisms become active to thus control the pathogenic organisms, the development of the disease in the early spring can certainly be suppressed. This corresponds to the idea of the dormant control. However, the diseases could not be controlled by the dormant spray of the conventional agricultural chemical comprising organic copper compound as a principal component. On the other hand, the organic copper preparation obtained in Example 4 shows a high controlling effect by the dormant spray thereof. This is a novel effect of the present invention which has not been accomplished, at all, by the conventional preparations mainly comprising organic copper compounds.

In addition, the organic copper agricultural chemical preparation obtained in Example 5 shows extremely high disease and/or insect-controlling effects as compared with the conventional agricultural pesticide mainly comprising organic copper compounds. More specifically, when the preparation obtained in Example 5 was sprayed in May, the development of melanose could be suppressed till October.

There was observed the same rate of disease-outbreak for the division, on which the conventional organic copper agricultural fungicide is sprayed, and the control division free of any treatment. The conventional organic copper agricultural chemical shows an effect of controlling melanose of citrus plants, but the mechanism thereof is such that the fungicide sprayed is adhered onto the plant's bodies and waits for scattered pathogenic organisms to suppress the growth thereof and to thus prevent the outbreak of the disease. However, if the chemical adhered to the plant's bodies is carried away by, for instance, raindrops, the effect is accordingly lost. The scattering of the pathogenic organisms is in general mediated by raindrops during rainfalls. For this reason, the efficacy of the conventional chemical only lasts a very short period of time. Contrary to this, the preparation obtained in Example 5 shows its effect through a mechanism different from that of the conventional chemical. More specifically, it directly acts on the pathogenic organisms which become a cause of the outbreak of diseases such as melanose and which are present on or within dead branches to thus control the same. Therefore, the preparation of Example 5 can suppress the outbreak of the disease over a very long time period. This is another novel effect of the present invention.

PREFERRED EMBODIMENTS FOR CARRYING OUT THE INVENTION

The present invention will hereinafter be specifically explained with reference to Preparation Examples in which the agricultural chemical preparations of the present invention are prepared, Test Examples in which the efficacy of the preparations are evaluated and Comparative Examples, but the present invention is not restricted to these specific Examples.

COMPARATIVE EXAMPLE 1

Glycerin monolaurate (20 parts by weight) was dissolved in 45 parts by weight of ethanol with warming at about 40° C., followed by addition of 20 parts by weight of copper sulfate, 10 parts by weight of citric acid and 20 parts by weight of HVP (hydrolyzate of vegetable proteins), immediate stirring and mixing of these ingredients to thus give a suspension concentrate. The preparation was stored in a sealed container immediately after the production thereof.

EXAMPLE 1

A wettable powder was prepared according to the following formulation.

| | |
|---|---|
| polyoxyethylene alkylallyl sulfoacetate | 20 parts by weight |
| glycerin monolaurate | 20 parts by weight |
| copper sulfate | 20 parts by weight |
| HVP (hydrolyzate of vegetable proteins) | 40 parts by weight |
| citric acid | 10 parts by weight |
| white carbon | 5 parts by weight |

Glycerin monolaurate (20 parts by weigth) was melted, with warming at about 40° C., along with 20 parts by weight of polyoxyethylene alkylallyl sulfoacetate. Separately, 20 parts by weight of copper sulfate and 10 parts by weight of citric acid were uniformly mixed with 40 parts by weight of HVP, followed by addition thereof to the foregoing warmed solution and uniform mixing. Then 5 parts by weight of white carbon was added to the resulting mixture and uniformly admixed to give a wettable powder.

The preparations of Example 1 and Comparative Example 1 were inspected for the disease preventing effects.

Test Methods
Angular Leaf Spot of Cucumber Plant

Each liquid formulation obtained by diluting the foregoing preparations to a desired concentration was sprayed on cucumber plant (variety: Suyo; 0.7 leaf stage) cultivated in an air conditioned greenhouse using spraying machinery. As a control, distilled water was sprayed on cucumber seedling in a division. Each liquid formulation was dried in a room, followed by inoculation, through spraying, of the cucumber seedling with *Pseudomonas syringae pv. lachrimams* cells which had been cultured in a PDA culture medium and then suspended in distilled water. After the inoculation, these test plants were held in a moist chamber (R.H. 100%) maintained at 25° C. and after 4 days, the number of lesions developed on the leaves was counted.

The preventive value of each preparation was evaluated on the basis of the following equation:

Preventive Value (%) = [1 − (number of lesions in treated division)/(number of lesions in untreated division)] × 100

Late Blight of Potato Plant

Each liquid formulation obtained by diluting the foregoing preparations to a desired concentration was sprayed on potato plant (variety: Danshaku; 5 to 7 leaf stage) cultivated in an air conditioned greenhouse using spraying machinery. As a control, distilled water was sprayed on potato plant in a division. Each liquid formulation was dried in a room, followed by inoculation, through spraying, of the potato plant with a suspension obtained by dipping and shaking leaves suffering from late blight, as an inoculum, in distilled water to thus suspend the pathogenic organisms therein. After the inoculation, these test plants were held in a moist chamber (R.H. 100%) maintained at 25° C. and after 4 days, the number of lesions developed on the leaves was counted.

The preventive value of each preparation was evaluated on the basis of the following equation:

Preventive Value (%) = [1 − (number of lesions in treated division)/(number of lesions in untreated division)] × 100

Bacterial Soft Rot of Lettuce Plant

Each liquid formulation obtained by diluting the foregoing preparations to a desired concentration was sprayed on lettuce plant grown in an air conditioned greenhouse till the number of true leaves reached about 5 using spraying machinery. As a control, distilled water was sprayed on lettuce plant in a division. Each liquid formulation was dried in a room, followed by inoculation, through spraying, of the lettuce plant with *Erwinia carotovora* subsp. *carotovora* cells which had been cultured in a PDA culture medium and then suspended in distilled water. After the inoculation, these test plants were held in a moist chamber (R.H. 100%) maintained at 25° C. and after 4 days, the area of leaves suffering from bacterial soft rot was determined.

The preventive value of each preparation was evaluated on the basis of the following equation:

Preventive Value (%) = [1 − (area of leaves suffering from bacterial soft rot in treated division)/(area of leaves suffering from the desease in untreated division)] × 100

Powdery Mildew of Cucumber Plant *Spaherothica fuliginea* cells were inoculated on seedlings of cucumber (variety: Sagami Hanjiro; 0.7 leaf stage) cultivated in an air conditioned greenhouse, followed by growing them in a greenhouse maintained at 25° C. for 7 to 10 days. After the development of the lesions of powdery mildew, each liquid formulation obtained by diluting the foregoing preparations to a desired concentration was sprayed on the leaves of the test plant using spraying machinery. As a control, distilled water was sprayed on cucumber plant in a division. Then the seedlings were again grown in a greenhouse and after 7 days from the spray of the agricultural chemical, it was judged whether lesions of powdery mildew present on each leaf were live or dead.

The preventive value was determined according to the following equation:

Preventive Value (%)=[(number of dead lesions)/(number of whole lesions)]×100

The results thus obtained are listed in the following Table 1.

TABLE 1

| | Preventing Effect (%) | | | | | |
|---|---|---|---|---|---|---|
| | Ex. 1 (ppm) | | | Comp. Ex. 1 (ppm) | | |
| Crop (Disease) | 50 | 100 | 200 | 50 | 100 | 200 |
| Immediately After Production of Preparations | | | | | | |
| Cucumber (Angular Leaf Spot) | 78 | 88 | 96 | 71 | 86 | 90 |
| Potato (Late Blight) | 82 | 100 | 100 | 77 | 95 | 100 |
| Lettuce (Bacterial Soft Rot) | 78 | 88 | 99 | 69 | 85 | 98 |
| Cucumber (Powder Mildew) | 91 | 100 | 100 | 80 | 92 | 99 |
| After 7 Days from Production of Preparations | | | | | | |
| Cucumber (Angular Leaf Spot) | 81 | 90 | 97 | 3 | 8 | 15 (Phyto. *) |
| Potato (Late Blight) | 85 | 100 | 100 | 12 | 31 | 51 (Phyto. *) |
| Lettuce (Bacterial Soft Rot) | 85 | 98 | 100 | 0 | 3 | 8 (Phyto. *) |
| Cucumber (Powder Mildew) | 89 | 100 | 100 | 35 | 52 | 68 (Phyto. *) |

Note: The preparation of Comparative Example 1 did not form an emulsion.
*: Phyto. = phytotoxicity.

DISCUSSION ON THE RESULTS OF COMPARATIVE EXAMPLE 1

The preparation of Example 1 showed a high preventing effect not only immediately after the production thereof, but also after one week from the production and the effect did not cause any reduction. The preparation of Example 1 was not deteriorated in its dispersibility required when preparing a spray even after one week from the production and accordingly, was easily dispersed. The preparation did not cause any phytotoxicity and was thus highly practical.

On the contrary, the preparation of Comparative Example 1 showed high preventing effect immediately after the production thereof, but was deteriorated in dispersibility after one week from the production, the preventing effect was extremely reduced. Moreover, the preparation was not uniformly dispersed and accordingly, caused phytotoxicity. Therefore, the comparative preparation was judged to be impractical.

COMPARATIVE EXAMPLE 2

Glycerin monolaurate (10 parts by weight) was dissolved in 40 parts by weight of ethanol with warming at about 40° C., followed by addition of 20 parts by weight of an HAP (hydrolyzate of animal proteins) solution, then 10 parts by weight of oxalic acid and 20 parts by weight of cupric chloride, stirring and mixing these ingredients to thus give a suspension concentrate.

EXAMPLE 2

A suspension concentrate was prepared according to the following formulation.

| | |
|---|---|
| calcium alkylbenzenesulfonate | 10 parts by weight |
| glycerin diacetomonolaurate | 10 parts by weight |
| cupric chloride | 20 parts by weight |
| adipic acid | 10 parts by weight |
| HAP (hydrolyzate of animal proteins) | 50 parts by weight |

To 10 parts by weigth of glycerin diacetomonolaurate, there were added 10 parts by weight of calcium alkylbenzene-sulfonate and then 50 parts by weight of an HAP solution and the mixture was dissolved with warming at a temperature of not more than 40° C. To the resulting mixture, there was added 10 parts by weight of adipic acid, followed by dissolving 20 parts by weight of cupric chloride in the resulting mixture and uniform mixing to give a suspension concentrate.

The preparations of Example 2 and Comparative Example 2 were inspected for the disease preventing effects according to the same test methods used in Example 1. The results thus obtained are listed in the following Table 2.

TABLE 2

| | Preventing Effect (%) | | | | | |
|---|---|---|---|---|---|---|
| | Ex. 2 (ppm) | | | Comp. Ex. 2 (ppm) | | |
| Crop (Disease) | 50 | 100 | 200 | 50 | 100 | 200 |
| Immediately After Production of Preparations | | | | | | |
| Cucumber (Angular Leaf Spot) | 80 | 88 | 100 | 68 | 80 | 90 |
| Potato (Late Blight) | 91 | 100 | 100 | 75 | 90 | 100 |
| Lettuce (Bacterial Soft Rot) | 85 | 92 | 99 | 66 | 78 | 89 |
| Cucumber (Powder Mildew) | 93 | 100 | 100 | 77 | 92 | 95 |
| After 7 Days from Production of Preparations | | | | | | |
| Cucumber | 88 | 95 | 97 | 5 | 11 | 17 (Phyto. *) |

TABLE 2-continued

| | Preventing Effect (%) | | | | | |
|---|---|---|---|---|---|---|
| | Ex. 2 (ppm) | | | Comp. Ex. 2 (ppm) | | |
| Crop (Disease) | 50 | 100 | 200 | 50 | 100 | 200 |
| (Angular Leaf Spot) | | | | | | |
| Potato (Late Blight) | 92 | 100 | 100 | 10 | 28 | 38 (Phyto. *) |
| Lettuce (Bacterial Soft Rot) | 90 | 98 | 100 | 0 | 5 | 10 (Phyto. *) |
| Cucumber (Powder Mildew) | 88 | 100 | 100 | 28 | 40 | 55 (Phyto. *) |

Note: The preparation of Comparative Example 2 did not form an emulsion.
*: Phyto. = phytotoxicity.

DISCUSSION ON THE RESULTS OF COMPARATIVE EXAMPLE 2

The preparation of Example 2 showed a high preventing effect not only immediately after the production thereof, but also after one week from the production and the effect did not cause any reduction. The preparation of Example 2 was not deteriorated in its dispersibility required when preparing a spray even after one week from the production and accordingly, was easily dispersed. The preparation did not cause any phytotoxicity and was thus highly practical.

On the contrary, the preparation of Comparative Example 2 showed high preventing effect immediately after the production thereof, but was deteriorated in dispersibility after one week from the production, the preventing effect was considerably reduced. Moreover, the preparation was not uniformly dispersed and accordingly, caused phytotoxicity. Therefore, the comparative preparation was judged to be impractical.

Separately, the citrus canker-preventing effects of the preparations of Examples 1 and 2 were compared with the effect of a commercially available inorganic copper preparation (Commercial Preparation).

Test Method

Leaves of citrus plants on which lesions of canker were formed were cut off and then immersed in each liquid formulation diluted to a desired concentration for 30 seconds. After air-drying the leaves, the leaves were suspended above potted citrus plant carrying young shoots and the plant was infected with this disease using an artificial raining device (10 mm/hr.). After the artificial rainfall for 3 hours, the plant was held in a moist chamber maintained at 25° C. for 2 days, followed by cultivation in a glass greenhouse and inspection of the plant for the extent of canker-development.

The preventive value (%) was determined according to the following equation:

Preventive Value (%) = [1 − (number of lesions in treated division)/(number of lesions in untreated division)] × 100

The results thus obtained are summarized in the following Table.

| Agricultural Chemical | Dilution | Controlling Effect (%) | Phytotoxicity |
|---|---|---|---|
| Preparation of Ex. 1 | ×200 | 96 | None |
| Preparation of Ex. 2 | ×200 | 97 | None |
| Commercial Preparation* | ×100 | 8 | severe |
| Control | — | 0 | None |

*Commercially available inorganic copper formulation.

Discussion and Comparison with Commercial Preparation

The preparations obtained in Examples 1 and 2 showed high preventing effects and they did not cause any phytotoxicity. Therefore, these preparations were proved to be highly practical.

On the contrary, the commercial inorganic copper preparation not only did not show any preventing effect, but also caused phytotoxicity of the young shoots. Therefore, the commercial preparation was proved to be impractical.

COMPARATIVE EXAMPLE 3

Glycerin monolaurate (20 parts by weight) was dissolved in 50 parts by weight of isopropyl alcohol with warming at a temperature of not more than 40° C., followed by addition of 70 parts by weight of sulfur powder to the resulting solution, stirring and mixing them to give a suspension concentrate.

EXAMPLE 3a

A suspension concentrate was prepared according to the following formulation.

| | |
|---|---|
| polyoxyethylene nonylphenyl ether | 20 parts by weight |
| glycerin monolaurate | 20 parts by weight |
| sulfur | 80 parts by weight |
| water | 40 parts by weight |

To 20 parts by weigth of glycerin monolaurate, there was added 20 parts by weight of polyoxyethylene nonylphenyl ether, followed by dissolution thereof with warming at a temperature of not more than 40° C. To the resulting solution, there was added 40 parts by weight of water, followed by sufficient stirring, addition of 80 parts by weight of sulfur powder and uniform mixing to give a suspension concentrate.

EXAMPLE 3b

A wettable powder was prepared according to the following formulation.

| | |
|---|---|
| polyoxyethylene nonylphenyl ether | 20 parts by weight |
| glycerin monolaurate | 20 parts by weight |
| sulfur | 60 parts by weight |
| white carbon | 20 parts by weight |

To 20 parts by weigth of glycerin monolaurate, there was added 20 parts by weight of polyoxyethylene nonylphenyl ether, followed by dissolution thereof with warming at a temperature of not more than 40° C. To the resulting solution, there was added 60 parts by weight of sulfur powder, followed by uniform mixing, addition of 20 parts by weight of white carbon and sufficient stirring to give a wettable powder.

The preparations obtained in Examples 3a and 3b and Comparative Example 3 were inspected for the disease preventing effects.

Powdery Mildew of Barley Plant

Barley plant (0.7 leaf stage) cultivated in an air-conditioned greenhouse were inoculated with spores of *Erysiohe graminis* and then held in a greenhouse maintained at 20° C. for 7 to 10 days. After development of powdery mildew lesions, each liquid formulation obtained by diluting the foregoing preparation to a desired concentration was sprayed on barley plant using spraying machinery. As a control, distilled water was sprayed on barley plant in a division. Then these test plant was again held in a greenhouse and after 7 days from the spray of the agricultural chemical, it was judged whether lesions of powdery mildew present on each leaf were live or dead.

The preventive value was determined according to the following equation:

Preventive Value (%)=[(number of dead lesions)/(number of whole lesions)]×100

Powdery Mildew of Cucumber

The test procedures used herein were the same as those described in Example 1.

Rust of Welsh Onion

Welsh onion plant (2 to 3 leaf stage) cultivated in an air-conditioned greenhouse were inoculated with the spores of *Puccinia allii* and then cultivated at 20° C. under high humidity conditions to thus generate rust lesions on the leaves of welsh onion.

Separately, one each of the foregoing infected welsh onion plant (inoculum) was placed at the center of a group of welsh onion plant (20 seedlings each; 2 to 3 leaf stage), followed by spraying the liquid formulation diluted to a desired concentration on these test plant using spraying machinery. As a control, distilled water was sprayed on welsh onion plant in a division. After spraying the liquid formulation, the test plant was isolated from one another, cultivated at 20° C. and under high humidity conditions to thus determine the number of rust lesions newly developed on the seedlings due to the infection through the inoculum.

The preventive value was determined according to the following equation:

Preventive Value (%) = [1 − (number of lesions in treated division)/

(number of lesions in untreated division)] × 100

Powdery Mildew of Vine Plant

Each liquid formulation obtained by diluting the foregoing preparations to a desired concentration was sprayed on fresh leaves of potted vine plant grown in a greenhouse using spraying machinery. As a control, distilled water was sprayed on the leaves of vine plant in a division. Each liquid formulation was dried in a room, followed by inoculation of the leaves of vine plant with spores of *Uncinula necator* by shaking leaves infected with powdery mildew above the test plant to thus scatter the spores of the organism. After the inoculation, these test plants were held in an air conditioned room maintained at 25° C. and after 10 days from the inoculation, the number of lesions developed on leaves was counted.

The preventive value of each preparation was evaluated on the basis of the following equation:

Preventive Value (%) = [1 − (number of lesions in treated division)/

(number of lesions in untreated division)] × 100

The results thus obtained are listed in the following Table 3.

TABLE 3

| | Preventing Effect (%) | | | | | | | | |
|---|---|---|---|---|---|---|---|---|---|
| | Ex. 3a (ppm) | | | Ex. 3b (ppm) | | | Comp. Ex. 3 (ppm) | | |
| Crop (Disease) | 50 | 100 | 200 | 50 | 100 | 200 | 50 | 100 | 200 |
| Immediately After Production of Preparations | | | | | | | | | |
| Barley (Powdery Mildew) | 87 | 100 | 100 | 100 | 100 | 100 | 68 | 84 | 98 |
| Cucumber (Powdery Mildew) | 88 | 100 | 100 | 98 | 100 | 100 | 72 | 92 | 99 |
| Welsh Onion (Rust) | 85 | 92 | 100 | 98 | 92 | 100 | 80 | 96 | 100 |
| Vine (Powdery Mildew) | 89 | 100 | 100 | 99 | 100 | 100 | 84 | 96 | 100 |
| After 7 Days from Production of Preparations | | | | | | | | | |
| Barley (Powdery Mildew) | 88 | 100 | 100 | 92 | 100 | 100 | 8 | 13 | 24 |
| Cucumber (Powdery Mildew) | 86 | 100 | 100 | 100 | 100 | 100 | 38 | 52 | 74 |
| Welsh Onion (Rust) | 88 | 100 | 100 | 99 | 100 | 100 | 0 | 5 | 12 |
| Vine (Powdery Mildew) | 84 | 100 | 100 | 98 | 100 | 100 | 0 | 9 | 35 |

Note: The preparation of Comparative Example 3 did not form an emulsion.

DISCUSSION ON THE RESULTS OF COMPARATIVE EXAMPLE 3

The preparations of Examples 3a and 3b showed high preventing effects not only immediately after the production thereof, but also after one week from the production and the effects did not cause any reduction. The preparations of Examples 3a and 3b were not deteriorated in the dispersibility required when preparing sprays even after one week from the production and accordingly, were easily dispersed. The preparations did not cause any phytotoxicity and were thus proved to be highly practical.

On the contrary, the preparation of Comparative Example 3 showed a high preventing effect immediately after the production thereof, but was deteriorated in dispersibility after one week from the production, the preventing effect was considerably impaired. Moreover, the preparation was not uniformly dispersed and accordingly, caused phytotoxicity. Therefore, the comparative preparation was judged to be impractical.

The cucumber powdery mildew-curative effects of the preparations of Examples 3a and 3b were compared with the effect observed for a commercially available sulfur preparation.

Test method

Seedlings of cucumber (variety: Sagami Hanjiro; 0.7 leaf stage) grown in an air-conditioned greenhouse were inoculated with spores of *Spaherothica fuliginea* and then held in a greenhouse maintained at 25° C. for 7 to 10 days. Each liquid formulation obtained by diluting the foregoing preparation to a desired concentration was sprayed on leaves carrying lesions of powdery mildew using a spraying machinery. As a control, distilled water was sprayed on the leaves of cucumber in a division. Thereafter, these test plants were again held in a greenhouse, the lesions of powdery mildew were cut off after 7 days from the spray of the preparation, followed by inoculation of seedlings of cucumber (variety: Sagami Hanjiro; 0.7 leaf stage) grown in an air-conditioned greenhouse with the spores by pressing the lesions against the true leaves of the seedlings. About 300 lesions were used for each inoculation. Thereafter, the test plants were held in a greenhouse maintained at 25° C. and each seedling was inspected for the outbreak of the disease after 10 days from the inoculation. If the outbreak of the disease was observed, the lesion was judged to have pathogenicity, while if the outbreak of the disease was not observed, the lesion was judged to be free of pathogenicity.

The curative effect was determined according to the following equation:

Curative Value (%) = [(number of lesions free of pathogenicity)/

(number of lesions used for inoculation)] × 100

| Agricultural Chemical | Concn. of S (ppm) | Lesions having Pathogenicity (A) | Lesions Free of Pathogenicity (B) | Effect of Curing: [B/(A + B)] × 100(%) |
|---|---|---|---|---|
| Prepapation of Example 3a | 50 | 0 | 286 | 100 |
| Prepapation of Example 3b | 50 | 0 | 225 | 100 |
| Commepcial S-Prepapation* | 100 | 161 | 126 | 44 |
| Commercial S-Prepapation* | 50 | 261 | 27 | 9 |
| Control | — | 305 | 0 | 0 |

*: Commercially available sulfur preparation.

DISCUSSION AND COMPARISON WITH COMMERCIALLY AVAILABLE SULFUR PREPARATION

All of the lesions of powdery mildew which were sprayed with the preparations obtained in Examples 3a and 3b lost their pathogenicity. More specifically, the preparations obtained in Examples 3a and 3b are proved to have an extremely high ability of curatively controlling powdery mildew.

On the contrary, the commercially available sulfur preparation was considerably inferior to the preparations of Examples 3a and 3b in the curative effect, i.e., curative effect of the former was found to be 44% even when it was used in an amount two times higher than those of the latter and 9% when used at the same concentration.

COMPARATIVE EXAMPLE 4

Glycerin monodioleate (40 parts by weight) was dissolved in 50 parts by weight of isopropyl alcohol with warming at a temperature of not more than 40° C., followed by addition of 20 parts by weight of citric acid and 20 parts by weight of copper 8-oxyquinoline, stirring and mixing them to give a suspension concentrate.

EXAMPLE 4

A suspension concentrate was prepared according to the following formulation:

| | |
|---|---|
| polyoxyethylene nonylphenyl ether | 10 parts by weight |
| glycerin monodioleate | 20 parts by weight |
| copper 8-oxyquinoline | 20 parts by weight |
| citric acid | 40 parts by weight |
| water | 40 parts by weight |

To 20 parts by weight of glycerin monodioleate, there was added 10 parts by weight of polyoxyethylene nonylphenyl ether, followed by dissolving with heating to a temperature of not more than 40° C. To the resulting solution, there was added 40 parts by weight of water, followed by sufficient stirring to give a uniform solution, mixing the solution with 40 parts by weight of citric acid, addition of 20 parts by weight of copper 8-oxyquinoline and uniform mixing of these ingredients to give a suspension concentrate.

Test on Disease-Control During Dormant Stage

The preparations obtained in Example 4 and Comparative Example 4 were inspected for the preventing effect.

Melanose of Citrus

Each preparation diluted to a desired concentration was sufficiently sprayed on citrus plant in a field early in March using a spraying machinery. As a control, distilled water was sprayed on the test plant in a division. Thereafter these plants were grown according to the usual manner without spraying any fungicide, followed by counting the number of melanose lesions present on 300 leaves per each preparation early in August.

The preventive value (%) was determined according to the following equation:

Preventive Value (%) = [1 − (number of lesions in treated division)/

(number of lesions in untreated division)] × 100

Canker of Citrus Plant

Each preparation diluted to a desired concentration was sufficiently sprayed on citrus plant in a field early in March using a spraying machinery. As a control, distilled water was sprayed on the test plant in a division. Thereafter these plants were cultivated according to the usual manner without spraying any fungicide, followed by counting the number of canker lesions present on 300 leaves per each preparation early in August.

The preventive value (%) was determined according to the following equation:

Preventive Value (%) = [1 − (number of lesions in treated division)/

(number of lesions in untreated division)] × 100

Anthracnose of Vine Trees

Each preparation diluted to a desired concentration was sufficiently sprayed on vine trees in a field in mid-March using a spraying machinery. As a control, distilled water was sprayed on the test plant in a division. Thereafter these plants were cultivated according to the usual manner without spraying any fungicide, followed by counting the number of anthracnose lesions present on 300 leaves per each preparation early in July.

The preventive value (%) was determined according to the following equation:

Preventive Value (%) = [1 − (number of lesions in treated division)/

(number of lesions in untreated division)] × 100

Black Spot of Pear Plant

Each preparation diluted to a desired concentration was sufficiently sprayed on pear trees in a field early in March using a spraying machinery. As a control, distilled water was sprayed on the test plant in a division. Thereafter these plants were cultivated according to the usual manner without spraying any fungicide, followed by counting the number of black spot lesions present on 300 leaves per each preparation early in July.

The preventive value (%) was determined according to the following equation:

Preventive Value (%) = [1 − (number of lesions in treated division)/

(number of lesions in untreated division)] × 100

The results thus obtained are summarized in the following Table 4.

preparation of Example 4 showed a high preventing effect during dormant stage as compared with the commercially available organic copper preparation.

Moreover, the mulberry plant dieback-preventing effect of the preparation obtained in Example 4 was compared with that observed for the commercially available organic copper preparation.

More specifically, each preparation diluted to a desired concentration was sufficiently sprayed on mulberry trees in a field late in October. Then the number of branches suffering from the disease was counted in next late April to thus determine the degree of damage (number of infected branches/whole number of branches present) for each test division.

The preventive value (%) was determined according to the following equation:

Preventive Value (%) = [1 − (degree of damage in treated division)/

(degree of damage in untreated division)] × 100

The results thus obtained are summarized in the following Table.

TABLE 4

| | Preventing Effect (%) | | | | | | |
|---|---|---|---|---|---|---|---|
| | Ex. 4 (ppm) | | | Comp. Ex. 4 (ppm) | | | Con. Ag. Med. |
| Crop (Disease) | 50 | 100 | 200 | 50 | 100 | 200 | 1000 ppm |
| | Immediately After Production of Preparations | | | | | | |
| Citrus (Melanose) | 78 | 100 | 100 | 28 | 49 | 95 | 18 |
| Citrus (Canker) | 98 | 100 | 100 | 85 | 92 | 100 | 0 |
| Vine (Anthracnose) | 75 | 92 | 100 | 48 | 75 | 80 | 25 |
| Pear (Black Spot) | 95 | 100 | 100 | 74 | 86 | 100 | 48 |
| | After 7 Days from Production of Preparations | | | | | | |
| Citrus (Melanose) | 80 | 92 | 100 | 0 | 5 | 22 | |
| Citrus (Canker) | 96 | 100 | 100 | 38 | 52 | 67 | |
| Vine (Anthracnose) | 77 | 96 | 100 | 2 | 8 | 17(Phyto.) | |
| Pear (Black Spot) | 98 | 100 | 100 | 44 | 56 | 80(Phyto.) | |

Note: The prepapation of Comparative Example 4 did not form an emulsion.
Con. Ag. Med.: Conventional Agricultural Chemical.
Phyto.: Phytotoxicity.

DISCUSSION ON THE RESULTS OF COMPARATIVE EXAMPLE 4

The preparation of Example 4 showed a high preventing effect not only immediately after the production thereof, but also after one week from the production and the effect did not cause any reduction. The preparation of Example 4 was not deteriorated in the dispersibility required when preparing a spray even after one week from the production and accordingly, was easily dispersed. The preparation did not cause any phytotoxicity and was thus proved to be highly practical.

On the contrary, the preparation of Comparative Example 4 showed a high preventing effect immediately after the production thereof, but was deteriorated in dispersibility after one week from the production, the preventing effect was considerably impaired. Moreover, the preparation was not uniformly dispersed and accordingly, caused phytotoxicity. Therefore, the comparative preparation was judged to be impractical.

By way of comparison, the same test was carried out using a commercially available organic copper preparation (the test was not carried out immediately after the production since the preparation was a commercial product). The

| Agricultural Chemical | Dilution | Degree of Damage (%) | Preventive Value (%) | Phytotoxicity |
|---|---|---|---|---|
| Preparation of Ex. 4 | ×100 | 5 | 94 | None |
| Commercial Organic Cu-Containing Ppepapation* | ×50 | 78 | 5 | severe |
| Untreated | — | 82 | 0 | None |

*: Altaber suspension concentrate (available from Tomono Agrica Co., Ltd.); effective component: copper 8-oxyquinoline.

COMPARISON WITH COMMERCIAL ORGANIC COPPER PREPARATION

The preparation of Example 4 not only exhibited a high prevente effect agaist mulberry plant die-back, but also did not cause any phytotoxicity.

Contrary to this, the commercial organic copper preparation not only showed a low preventing effect, but also caused phytotoxicity.

COMPARATIVE EXAMPLE 5

Glycerin monocaprylate (80 parts by weight) was dissolved in 80 parts by weight of isopropyl alcohol with heating to a temperature of not more than 40° C., followed by addition of 40 parts by weight of copper 8-oxyquinoline, stirring and mixing of these ingredients to give a suspension concentrate.

EXAMPLE 5

A wettable powder was prepared according to the following formulation:

| | |
|---|---|
| polyoxyethylene alkyl ether | 40 parts by weight |
| glycerin monocaprylate | 40 parts by weight |
| copper 8-oxyquinoline | 80 parts by weight |
| lactose | 30 parts by weight |

To 80 parts by weight of glycerin monocaprylate, there was added 40 parts by weight of polyoxyethylene alkyl ether, followed by dissolution thereof with heating at a temperature of not more than 40° C. Then there were added, to the resulting solution, 40 parts by weight of copper 8-oxyquinoline and 30 parts by weight of lactose and these ingredients were uniformly admixed together to give a wettable powder.

TEST ON DISEASE-CONTROL DURING VEGETATION PERIOD

The preparations of Example 5 and Comparative Example 5 were inspected for the preventing effects.
Test Method
Melanose of Citrus Each preparation diluted to a desired concentration was sufficiently sprayed on citrus plant in a field in mid-May using a spraying machinery. As a control, distilled water was sprayed on the test plant in a division. Thereafter these plants were grown according to the usual manner without spraying any fungicide, followed by counting the number of melanose lesions present on 300 leaves per each preparation early in October.

The preventive value (%) was determined according to the following equation:

Preventive Value (%) =
[1 − (number of lesions in treated division)/(number of lesions in untreated division)] × 100

Canker of Citrus Plant

Each preparation diluted to a desired concentration was sufficiently sprayed on citrus plant in a field in mid-May using a spraying machinery. As a control, distilled water was sprayed on the test plant in a division. Thereafter these plants were cultivated according to the usual manner without spraying any fungicide, followed by counting the number of canker lesions present on 300 leaves per each preparation early in October.

The preventive value (%) was determined according to the following equation:

Preventive Value (%) =
[1 − (number of lesions in treated division)/(number of lesions in untreated division)] × 100

Anthracnose of Vine Trees

Each preparation diluted to a desired concentration was sufficiently sprayed on vine trees in a field late in April using a spraying machinery. As a control, distilled water was sprayed on the test plant in a division. Thereafter these plants were cultivated according to the usual manner without spraying any fungicide, followed by counting the number of anthracnose lesions present on 300 leaves for each preparation early in October.

The preventive value (%) was determined according to the following equation:

Preventive Value (%) =
[1 − (number of lesions in treated division)/(number of lesions in untreated division)] × 100

Black Spot of Pear Plant

Each preparation diluted to a desired concentration was sufficiently sprayed on pear trees in a field early in May using a spraying machinery. As a control, distilled water was sprayed on the test plant in a division. Thereafter these plants were cultivated according to the usual manner without spraying any fungicide, followed by counting the number of black spot lesions present on 300 leaves for each preparation early in October.

The preventive value (%) was determined according to the following equation:

Preventive Value (%) =
[1 − (number of lesions in treated division)/(number of lesions in untreated division)] × 100

The results thus obtained are summarized in the following Table 5.

TABLE 5

| | Preventing Effect (%) | | | | | |
|---|---|---|---|---|---|---|
| | Ex. 5 (ppm) | | | Comp. Ex. 5 (ppm) | | |
| Crop (Disease) | 50 | 100 | 200 | 50 | 100 | 200 |
| Immediately After Production of Preparations | | | | | | |
| Citrus (Melanose) | 99 | 100 | 100 | 79 | 88 | 98 |
| Citrus (Canker) | 87 | 100 | 100 | 78 | 95 | 100 |
| Vine (Anthracnose) | 88 | 96 | 100 | 80 | 94 | 100 |
| Pear (Black Spot) | 95 | 100 | 100 | 78 | 89 | 99 |
| After 7 Days from Production of Preparations | | | | | | |
| Citrus (Melanose) | 98 | 100 | 100 | 6 | 15 | 22 (Phyto.) |
| Citrus (Canker) | 91 | 100 | 100 | 0 | 8 | 28 (Phyto.) |
| Vine (Anthracnose) | 94 | 99 | 100 | 3 | 16 | 18 (Phyto.) |
| Pear (Black Spot) | 96 | 100 | 100 | 18 | 26 | 45 (Phyto.) |

Note: The preparation of Comparative Example 5 did not form an emulsion. Phyto.: Phytotoxicity.

DISCUSSION ON THE RESULTS OF COMPARATIVE EXAMPLE 5

The preparation of Example 5 showed a high preventing effect not only immediately after the production thereof, but also after one week from the production and the effect did not cause any reduction. The preparation of Example 5 was not deteriorated in the dispersibility required when preparing a spray even after one week from the production and accordingly, was easily dispersed. The preparation did not cause any phytotoxicity and was thus proved to be highly practical.

On the contrary, the preparation of Comparative Example 5 showed a high preventing effect immediately after the production thereof, but was deteriorated in dispersibility after one week from the production, the preventing effect was considerably impaired. Moreover, the preparation was not uniformly dispersed and accordingly, caused phytotoxicity. Therefore, the comparative preparation was judged to be impractical.

Moreover, the preventive effect of the preparation obtained in Example 5 against Citrus Melanose was compared with that observed for the commercially available organic copper preparation.

Test Method

Each preparation diluted to a desired concentration was sprayed on citrus trees in a field late in May. Then the cultivation of these citrus trees were continued and the test plants were inspected for the degree of damage on October to thus determine the preventive value. The results thus obtained are listed in the following Table.

| Agricultural Chemical | Concn. (ppm) | Preventive Value (%) | Phyto-toxicity |
|---|---|---|---|
| Preparation of Ex. 5 | 200 | 98 | — |
| Commercial Organic Copper Preparation* | 1000 | 12 | — |
| Untreated | — | 0 | — |

*: Oxynedo 80 (available from Tomono Agrica Co., Ltd.); effective component: copper 8-oxyquinoline.

COMPARISON WITH COMMERCIAL ORGANIC COPPER PREPARATION

The effect of the preparation of Example 5 was compared with that observed for the commercial organic copper preparation. As a result, it was found that the former exhibited a high preventing effect, but the latter showed an extremely low preventing effect.

Dispersibility Test

The preparation of Example 2 and that (E-14) prepared by the method described in Example 14 of J. P. KOKAI No. Sho 63-233902 each was introduced into a glass bottle, stored in sealed or opened states and periodically inspected for the formation of an emulsion (dispersibility). The results thus obtained are listed in Table 6.

TABLE 6

| Days After Production | Preparation of Ex. 2 | | Preparation E-14 | |
|---|---|---|---|---|
| | Sealed | Opened | Sealed | Opened |
| The Day of Production | ⊚ | ⊚ | ⊚ | ⊚ |
| After One Day | ⊚ | ⊚ | ⊚ | ○ |
| After 3 Days | ⊚ | ⊚ | ○ | Δ |
| After 7 Days | ⊚ | ⊚ | Δ | x |
| After 14 Days | ⊚ | ⊚ | Δ | x |
| After 30 Days | ⊚ | ⊚ | x | x |
| After 60 Days | ⊚ | ⊚ | x | x | x: The emulsion formation was insufficient.
Δ: The emulsion formation was rather insufficient.
○: The emulsion formation was rather satisfied.
⊚: The emulsion was satisfactorily formed.

The preparation of Example 4 and that (E-16) prepared by the method described in Example 16 of J. P. KOKAI No. Sho 63-233902 each was introduced into a glass bottle, stored in sealed or opened states and periodically inspected for the formation of an emulsion (dispersibility). The results thus obtained are listed in Table 7.

TABLE 7

| Days After Production | Preparation of Ex. 4 | | Preparation E-16 | |
|---|---|---|---|---|
| | Sealed | Opened | Sealed | Opened |
| The Day of Production | ⊚ | ⊚ | ⊚ | ⊚ |
| After 3 Days | ⊚ | ⊚ | ⊚ | Δ |

TABLE 7-continued

| Days After Production | Preparation of Ex. 4 | | Preparation E-16 | |
|---|---|---|---|---|
| | Sealed | Opened | Sealed | Opened |
| After 7 Days | ⊚ | ⊚ | ○ | x |
| After 30 Days | ⊚ | ⊚ | x | x | x: The emulsion formation was insufficient.
Δ: The emulsion formation was rather insufficient.
○: The emulsion formation was rather satisfied.
⊚: The emulsion was satisfactorily formed.

I claim:

1. An agricultural chemical preparation comprising 100 parts by weight of a fatty acid ester of an aliphatic polyhydric alcohol, 10 to 2000 parts by weight of powdery sulfur and 10 to 400 parts by weight of a nonionic surfactant selected from the group consisting of polyoxyethylene alkyl ether, polyoxyethylene alkylallyl ether, polyoxyethylene alkylphenyl ether, polyoxyethylene alkylamine, alkyldihydroxyalkylamine, polyoxyethylene bisphenyl ether and polyoxyethylene alkyl ester.

2. The agricultural chemical preparation of claim 1 wherein said surfactant is selected from the group consisting of polyoxyethylene alkyl ether, polyoxyethylene alkylallyl ether, and polyoxyethylene alkylphenyl ether.

3. The agricultural chemical preparation of claim 1 wherein said surfactant is polyoxyethylene alkylphenyl ether.

4. The agricultural chemical preparation of claim 1 wherein said fatty acid ester of an aliphatic polyhydric alcohol is glycerin monolaurate.

5. The agricultural chemical preparation of claim 1 wherein the powdery sulfur comprises fine particles that at least pass through 200 mesh.

6. The agricultural chemical preparation of claim 1 wherein the content of the powdery sulfur ranges from 10 to 60% by weight of the total weight of the agricultural chemical preparation.

7. A method for controlling and/or treating a plant disease selected from the group consisting of powdery mildew and rust, which comprises the steps of providing an agricultural chemical preparation comprising 100 parts by weight of a fatty acid ester of an aliphatic polyhydric alcohol, 10 to 2000 parts by weight of powdery sulfur and 10 to 400 parts by weight of a nonionic surfactant selected from the group consisting of polyoxyethylene alkyl ether, polyoxyethylene alkylallyl ether, polyoxyethylene alkylphenyl ether, polyoxyethylene alkylamine, alkyldihydroxyalkylamine, polyoxyethylene bisphenyl ether and polyoxyethylene alkyl ester; and applying the agricultural chemical preparation to a plant suffering from the disease.

8. The method of claim 7 wherein the plant disease is selected from the group consisting of powdery mildew of cucumber, powdery mildew of barley plant, powdery mildew of vine plant and rust of Welsh onion.

9. The method of claim 7 wherein said surfactant is selected from the group consisting of polyoxyethylene alkyl ether, polyoxyethylene alkylallyl ether, and polyoxyethylene alkylphenyl ether.

10. The method of claim 7 wherein said surfactant is polyoxyethylene alkylphenyl ether.

11. The method of claim 7 wherein said fatty acid ester of an aliphatic polyhydric alcohol is glycerin monolaurate.

12. The method of claim 7 wherein the powdery sulfur comprises fine particles of not less than 200 mesh pass.

13. The method of claim 7 wherein the content of the powdery sulfur ranges from 10 to 60% by weight of the total weight of the agricultural chemical preparation.

* * * * *